(12) United States Patent
Martin et al.

(10) Patent No.: US 8,894,692 B2
(45) Date of Patent: *Nov. 25, 2014

(54) PEDICLE SCREW ASSEMBLY AND METHODS THEREFOR

(75) Inventors: Greg Martin, Carlsbad, CA (US); Yves Stephane Crozet, Ramsey, NJ (US); William J. Kelly, Montville, NJ (US)

(73) Assignee: Stryker France (FR)

( * ) Notice: Subject to any disclaimer, the term of this patent is extended or adjusted under 35 U.S.C. 154(b) by 256 days.

This patent is subject to a terminal disclaimer.

(21) Appl. No.: 13/243,322

(22) Filed: Sep. 23, 2011

(65) Prior Publication Data

US 2012/0071932 A1    Mar. 22, 2012

Related U.S. Application Data

(63) Continuation of application No. 11/303,091, filed on Dec. 15, 2005, now Pat. No. Re. 42,932, which is an application for the reissue of Pat. No. 6,858,030, which is a continuation of application No. 09/755,846, filed on Jan. 5, 2001, now Pat. No. 6,488,681.

(51) Int. Cl.
*A61B 17/88* (2006.01)
*A61B 17/70* (2006.01)

(52) U.S. Cl.
CPC ......... *A61B 17/7037* (2013.01); *A61B 17/7082* (2013.01); *A61B 17/7032* (2013.01)
USPC .......................... 606/279; 606/278; 606/86 A

(58) Field of Classification Search
CPC ........... A61B 17/7037; A61B 17/7032; A61B 17/7082
USPC ......... 606/266, 272, 76, 279, 86 A, 278, 264, 606/70, 71, 301, 305, 328, 269
See application file for complete search history.

(56) References Cited

U.S. PATENT DOCUMENTS

| | | | |
|---|---|---|---|
| 5,067,955 A | 11/1991 | Cotrel et al. | |
| 5,129,388 A | 7/1992 | Vignaud et al. | |
| 5,246,442 A | 9/1993 | Ashman et al. | |
| 5,253,406 A | 10/1993 | Shere et al. | |
| 5,466,237 A * | 11/1995 | Byrd et al. | 606/272 |
| 5,474,555 A | 12/1995 | Puno et al. | |

(Continued)

FOREIGN PATENT DOCUMENTS

| | | |
|---|---|---|
| DE | 195 42 116 | 5/1997 |
| WO | 96/08206 | 3/1996 |
| WO | 00/72769 | 12/2000 |

*Primary Examiner* — Pedro Philogene
(74) *Attorney, Agent, or Firm* — Lerner, David, Littenberg, Krumholz & Mentlik, LLP

(57) ABSTRACT

A method for stabilizing a spine includes providing a coupling element having upper and lower ends, a rod receiving opening adapted to receive an elongated stabilizing rod, a bore extending through the lower end and a seat surrounding the bore adjacent the lower end; providing a fastener having upper and lower ends, a head having a radial surface, and at least one anchoring element between the lower end of the fastener and the head; assembling the fastener with the coupling element; anchoring the fastener to bone; moving the coupling element relative to the fastener for capturing the elongated stabilizing rod in the rod receiving opening; and urging the captured stabilizing rod toward the head of the fastener so that the rod contacts the head and forces the radial surface of the head against the seat.

20 Claims, 11 Drawing Sheets

(56) References Cited

U.S. PATENT DOCUMENTS

| | | | |
|---|---|---|---|
| 5,476,464 A | 12/1995 | Metz-Stavenhagen et al. | |
| 5,554,157 A | 9/1996 | Errico et al. | |
| 5,669,911 A | 9/1997 | Errico et al. | |
| 5,672,176 A | 9/1997 | Biedermann et al. | |
| 5,690,630 A | 11/1997 | Errico et al. | |
| 5,733,286 A | 3/1998 | Errico et al. | |
| 5,797,911 A | 8/1998 | Sherman et al. | |
| 5,817,094 A | 10/1998 | Errico et al. | |
| 5,879,350 A | 3/1999 | Sherman et al. | |
| 5,882,350 A | 3/1999 | Ralph et al. | |
| 5,885,286 A | 3/1999 | Sherman et al. | |
| 5,946,988 A * | 9/1999 | Metz-Stavenhagen | 81/111 |
| 5,951,553 A | 9/1999 | Betz et al. | |
| 6,013,601 A | 1/2000 | Gundjian et al. | |
| 6,030,389 A | 2/2000 | Wagner et al. | |
| 6,045,554 A | 4/2000 | Grooms et al. | |
| 6,053,917 A | 4/2000 | Sherman et al. | |
| 6,063,090 A | 5/2000 | Schlapfer et al. | |
| 6,074,391 A * | 6/2000 | Metz-Stavenhagen et al. | 606/278 |
| 6,077,262 A * | 6/2000 | Schlapfer et al. | 606/305 |
| 6,090,110 A | 7/2000 | Metz-Stavenhagen et al. | |
| 6,090,111 A | 7/2000 | Nichols | |
| 6,113,601 A | 9/2000 | Tatar | |
| 6,132,434 A | 10/2000 | Sherman et al. | |
| 6,254,602 B1 * | 7/2001 | Justis | 606/272 |
| 6,280,442 B1 * | 8/2001 | Barker et al. | 606/60 |
| RE37,665 E | 4/2002 | Ralph et al. | |
| 6,443,953 B1 * | 9/2002 | Perra et al. | 606/270 |
| 6,485,491 B1 | 11/2002 | Farris | |
| 6,488,681 B2 * | 12/2002 | Martin et al. | 606/278 |
| 6,540,748 B2 | 4/2003 | Lombardo | |
| RE42,932 E * | 11/2011 | Martin et al. | 606/278 |

* cited by examiner

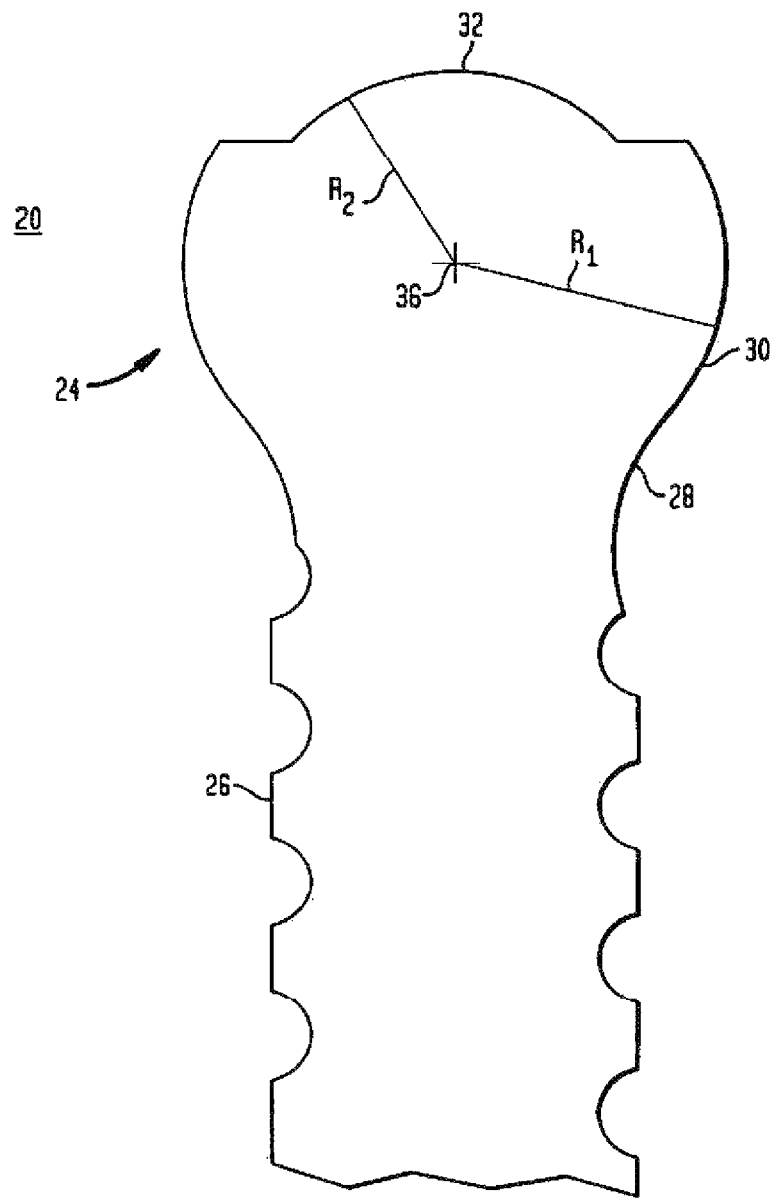

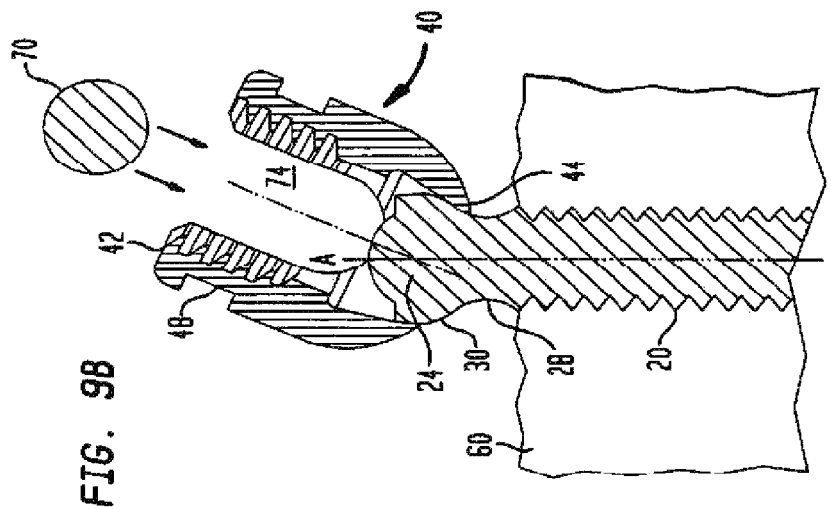
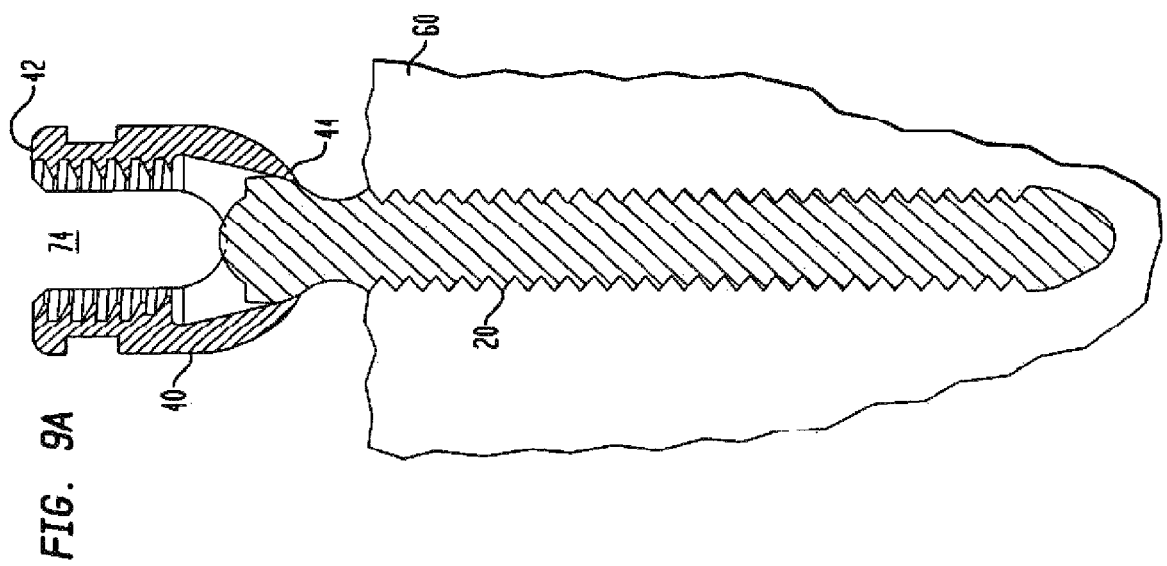

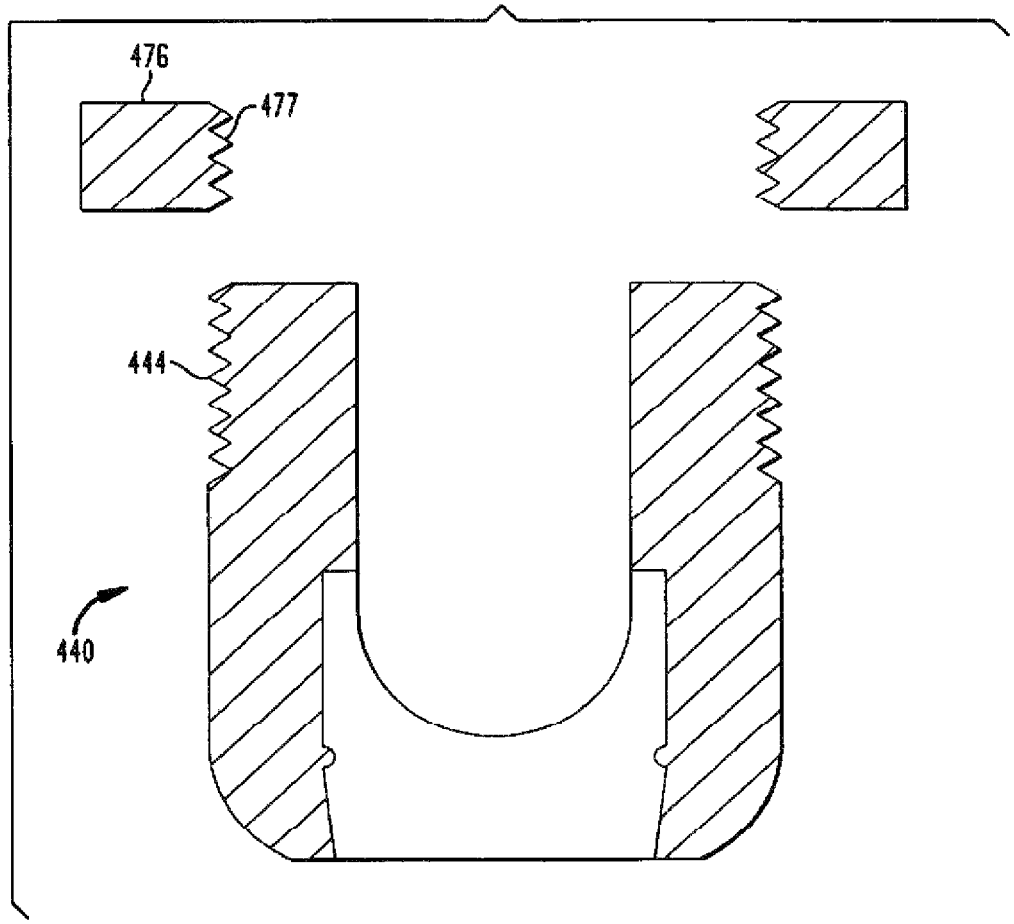

PEDICLE SCREW ASSEMBLY AND METHODS THEREFOR

CROSS REFERENCE TO RELATED APPLICATIONS

This application is a continuation of U.S. application Ser. No. 11/303,091 filed Dec. 15, 2005, which is a reissue of Ser. No. 10/197,092 filed Jul. 17, 2002, now U.S. Pat. No. 6,858,030, which is a continuation of U.S. application Ser. No. 09/755,846 filed Jan. 5, 2001, now U.S. Pat. No. 6,488,681.

BACKGROUND OF THE INVENTION

The present invention relates generally to spinal fixation devices and more specifically relates to a pedicle screw assembly having a low profile and having an improved screwhead/coupling element interface for locking the assembly.

The spinal column is a highly complex system of bones and connective tissues that provides support for the body and protects the delicate spinal cord and nerves. The spinal column includes a series of vertebrae stacked one atop the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

The present invention generally involves a technique commonly referred to as spinal fixation whereby surgical implants are used for fusing together and/or mechanically immobilizing vertebrae of the spine. Spinal fixation may also be used to alter the alignment of adjacent vertebrae relative to one another so as to change the overall alignment of the spine. Such techniques have been used effectively to treat the above-described conditions and, in most cases, to relieve pain suffered by the patient. However, as will be set forth in more detail below, there are some disadvantages associated with current fixation devices.

One spinal fixation technique involves immobilizing the spine by using orthopedic rods, commonly referred to as spine rods, that run generally parallel to the spine. This may be accomplished by exposing the spine posteriorly and fastening bone screws to the pedicles of the appropriate vertebrae. The pedicle screws are generally placed two per vertebra and serve as anchor points for the spine rods. Clamping elements adapted for receiving a spine rod therethrough are then used to join the spine rods to the screws. The aligning influence of the rods forces the spine to conform to a more desirable shape. In certain instances, the spine rods may be bent to achieve the desired curvature of the spinal column.

U.S. Pat. No. 5,129,388 to Vignaud et al. discloses a spinal fixation device including a pedicle screw having a U-shaped head rigidly connected to an upper end of the screw. The U-shaped head includes two arms forming a U-shaped channel for receiving a spine rod therein. The U-shaped head is internally threaded so that a set screw having external threads may be screwed therein. After the pedicle screw has been inserted into bone and a spine rod positioned in the U-shaped channel, the set screw is threaded into the internal threads of the U-shaped channel for securing the spine rod in the channel and blocking relative movement between the spine rod and the pedicle screw. The fixation device also includes a cap covering an upper portion of the U-shaped head to prevent the arms from spreading upon threading the set screw into the internal threads of U-shaped head.

Surgeons have encountered considerable difficulty when attempting to insert spinal fixation devices such as those disclosed in the above-mentioned '388 patent. This is because the U-shaped heads of adjacent screws are often out of alignment with one another due to curvature in spines and the different orientations of the pedicles receiving the screws. As a result, spine rods must often be bent in multiple planes in order to pass the rods through adjacent U-shaped channels. These problems weaken the strength of the assembly and result in significantly longer operations, thereby increasing the likelihood of complications associated with surgery.

In response to the above-noted problems, U.S. Pat. No. 5,733,286 to Errico et al., U.S. Pat. No. 5,672,176 to Biedermann et al., and U.S. Pat. No. 5,476,464 to Metz-Stavenhagen disclose polyaxial spinal fixation devices wherein the anchoring element fixed to the bone has a spherically-shaped head. The fixation devices in the above-identified patents also have orthopedic rod capturing assemblies for securing orthopedic rods in the capturing assemblies and connecting the rods with the anchoring elements. The spherically-shaped heads of the anchoring elements permit movement of the anchoring elements relative to the orthopedic rod capturing assemblies. However, the above-mentioned patents do not solve all of the deficiencies of fixation devices such as those described in the Vignaud '388 patent because the respective spinal fixation devices may shift following insertion. This is due primarily to the fact that there is insufficient surface area contact between the spherically-shaped heads of the anchoring elements and the rod capturing assemblies. In addition, the devices are complex, include many parts, and are difficult to manufacture.

In certain preferred embodiments of commonly assigned U.S. patent application Ser. No. 09/414,272, filed Oct. 7, 1999, the disclosure of which is hereby incorporated by reference as if fully set forth herein, a pedicle screw assembly includes a fastener having a tip end for insertion into bone and an expandable head at the opposite end of the fastener. The expandable head has an outer surface including a convex portion, a recess having an inner surface and defining an inner dimension, and at least one slot extending between the inner and outer surfaces thereof for allowing expansion of the head. The assembly also has an insert which can be positioned at least partially in the recess, the insert having an outer surface and defining an outer dimension that is greater than the inner dimension of the recess. The assembly includes a coupling element having a rod receiving opening, a bore for receiving the fastener, and a seat for receiving the head of the fastener, the seat including a concave portion for receiving the convex underside of the head and allowing the fastener to pivot and rotate relative to the coupling element before being locked therein. After an orthopedic rod has been positioned within the coupling element, a locking element associated with the coupling element locks the orthopedic rod in the rod-receiving opening. The locking element is adapted to be forced against an orthopedic rod arranged in the rod receiving opening, to in turn force the insert into the recess of the expandable head so that the outer dimension of the insert bears against the inner dimension of the head, thereby expanding the outer surface of the head against the concave seat of the coupling element for locking the fastener from further pivotal movement relative to the coupling element. In other preferred embodiments, the head is expandable by virtue of the material of which it is made, such as carbon fiber.

In spite of the above-mentioned devices, there remains room for improvement of prior art spinal fixation devices in the manner of locking the screwhead, the complexity of use, difficulty in properly positioning the orthopedic rod and the rod-capturing assemblies, the required manipulation of the many parts associated with some complex devices and postoperative movement of the rod-capturing assemblies relative to the bone anchoring elements due to the weak interfaces between the two.

SUMMARY OF THE INVENTION

In accordance with certain preferred embodiments of the present invention, a stabilizing assembly used for stabilizing a spinal column includes a fastener having an upper end and a head at the upper end, and at least one anchoring element between the upper and lower ends thereof. The head of the fastener preferably includes a center, an underside including a first radial surface and a top side including a second radial surface, the first radial surface defining a first radius from the center of the head and the second radial surface defining a second radius from the center of the head, the first radius being greater than the second radius. Although the present invention is not limited by any particular theory of operation, it is believed that utilizing a fastener head having a dual-radius outer surface will provide a stabilizing assembly having a lower overall silhouette, thereby enhancing the compactness of the assembly. The lower silhouette results, in part, from the lower height of the second radial surface at the top of the head.

The pedicle screw assembly also preferably includes a coupling element that couples together the fastener and a stabilizing rod inserted into the coupling element. The coupling element desirably includes an upper end and a lower end, a rod receiving opening adapted to receive a stabilizing rod, a bore extending through the lower end of the coupling element for receiving the fastener, and a seat adjacent the lower end of the coupling element adapted to engage the first radial surface of the head when the fastener is positioned in the bore. In certain preferred embodiments the seat is a conical-shaped seat having side walls that taper inwardly toward the lower end of the coupling element. In certain preferred embodiments, the rod-receiving opening begins at the upper end of the coupling element and extends toward the lower end of the coupling element, the lower end of the rod-receiving opening preferably terminating at U-shaped channels on opposite sides of the coupling element.

The stabilizing assembly also preferably includes a locking element associated with the coupling element, the locking element being adapted to apply a force upon a stabilizing rod positioned in the rod receiving opening, whereby the stabilizing rod in turn applies a force upon the second radial surface of the head for forcing the first radial surface of the head against the conical-shaped seat for preventing further pivotal and rotational movement of the fastener and the coupling element relative to one another. The locking element may include a set screw having external threads for threadably engaging internal threads of the coupling element. However, in other embodiments, the coupling element preferably includes external threads formed on an exterior surface of the coupling element and the locking element includes a nut having internal threads threadable onto the external threads of the coupling element.

In certain preferred embodiments, the fastener is a screw fastener having a longitudinal axis extending between the upper and lower ends thereof, and includes a screwhead having at least one groove extending from the top surface of the screwhead toward the underside of the screwhead, the at least one groove being adapted to receive a driver for inserting the fastener into bone. The at least one groove preferably extends in a direction substantially parallel to the longitudinal axis of the fastener. Moreover, the at least one groove desirably includes a plurality of grooves that are equally spaced apart from one another about the head. The fastener also preferably includes a neck portion having a reduced diameter for facilitating pivotal movement of the coupling element and the fastener relative to one another. The neck of the fastener may also have a concave surface so as to broaden the pivotal range of the fastener relative to the coupling element.

The fastener may be inserted into bone using a driver including a shaft having a lower end and a plurality of prongs extending from the lower end of the shaft. The prongs are preferably adapted for being inserted into the grooves of the head. The shaft of the driver may include external threads that are adapted for engaging the internal threads of the coupling element.

In operation, the coupling element is anchored in place by anchoring the screw fastener into bone, such as vertebral bone. A pilot hole may be formed in the bone before the fastener is anchored to the bone. After the coupling element is anchored in place, a gap preferably remains between the lower end of the coupling element and the bone so that the coupling element is free to pivot and rotate relative to the fastener and bone. This pivoting and rotary action facilitates the positioning of an orthopedic stabilizing rod within the rod-receiving opening of the coupling element.

After a stabilizing rod has been positioned in the rod-receiving opening of the coupling element, the locking element, i.e., an externally threaded set screw, is threaded into the internal threads of the coupling element. As the set screw is tightened, the underside of the set screw abuts the orthopedic rod to apply a downward force through the rod onto the second radial surface of the head. As used herein, the term "downward force" means a force directed toward the lower end of the coupling element. The downward force applied to the second radial surface of the head forces the first radial surface of the head into the conical-shaped seat of the coupling element. Engagement of the first radial surface of the screwhead with the conical-shaped seat locks the coupling element relative to the screwhead, thereby preventing further pivotal and rotary movement of the coupling element. As a result, the likelihood of post-operative shifting and/or movement of a spine rod or coupling element relative to one or more of the bone fasteners is significantly reduced. Thus, the present invention provides for a more reliable spinal fixation device and overcomes the post-operative shifting problems seen in prior art devices. Moreover, the pedicle screw assembly of the present invention has fewer parts. As a result, implantation operations are greatly simplified and the possibility of a component being dropped inside a patient's body greatly reduced.

In certain preferred embodiments, the fastener may have one or more holes therein for receiving bone graft material as disclosed in U.S. Pat. No. 4,484,570 to Sutter. Instead of using a screw for securing the screw to bone, in other preferred embodiments the fastener may include a hook-shaped anchoring element as disclosed in the above-mentioned U.S. Pat. No. 5,476,464 to Metz-Stavenhagen. The fastener may also be a structure having barbs on an outer surface thereof, whereby the fastener is forced into bone and the barbs prevent the fastener from being withdrawn from the bone.

In certain preferred embodiments, the top surface of the fastener head may include a socket adapted to receive a driver, such as a screwdriver or a hexagonal wrench. In this embodiment, the fastener is attached to bone by inserting the driver into the socket, and then turning the driver to rotate the fastener in either a clockwise or counterclockwise direction.

The coupling element may also have one or more impressions or grooves formed therein for receiving a controlling device, such as a persuader instrument for seating the rod in the coupling element. In some embodiments, the impressions or grooves generally extend in a direction substantially perpendicular to the longitudinal axis of the coupling element. The groove or blind holes may be formed in the exterior surface of the coupling element.

The interior surface of the coupling element at the lower end thereof preferably defines the seat adapted for engaging the first radial surface at the underside of the head and for allowing the head to pivot relative to the coupling element before being locked in place. The seat is preferably provided adjacent the lower end of the coupling element. The seat may define a conical shape or a convex shape. In particular preferred embodiments, the seat is a conical-shaped seat. The walls of the conical-shaped seat preferably taper inwardly toward one another so that the diameter of the walls at the lower end thereof is less than the outer diameter of the head.

During assembly of the above-mentioned stabilizing device, a portion of the fastener is passed through the bore of the coupling element until the underside of head is positioned adjacent the conical-shaped seat of the coupling element. During a spinal fixation operation, after the fastener has been anchored in bone, the coupling element remains free to pivot relative to the fastener. Moreover, a gap preferably exists between the bottom of the coupling element and bone, the presence of the gap facilitating pivoting movement of the coupling element. The neck portion of the fastener, preferably having a concave surface with a diameter less than the diameter of the threaded portion of the fastener, enables the coupling element to pivot through a broader range of angles relative to the fastener. Thus, a spine rod may be more easily positioned within the rod receiving opening of the coupling element. After the rod has been positioned within the rod receiving opening, a locking element is threaded into the threads of the coupling element. As the locking element tightens down upon the rod, the rod, in turn, exerts a downward force onto the second radial surface of the head. The downward force applied to the second radial surface of the head forces the first radial surface of the head into the conical-shaped seat of the coupling element. Engagement of the first radial surface of the head with the conical-shaped seat locks the coupling element relative to the head, thereby preventing further pivotal and rotary movement of the coupling element. As a result, the likelihood of post-operative shifting and/or moving of the pedicle screw assembly is greatly reduced, thereby minimizing the occurrence of post-operative complications for spinal implant patients.

The present invention also preferably includes a tool for securing or anchoring the fastener in bone. The tool is preferably a driver having a rotatable shaft and one or more prongs extending from an end of the shaft for engaging grooves in the head. In preferred embodiments, the driver has one prong for each groove in the head of the fastener. The driver may also have external threads at a lower end of the shaft. The external threads are preferably adapted for engaging the internal threads of the coupling element when a fastener is being anchored to the bone. The engagement of the external threads of the driver and the internal threads of the coupling element generally stabilizes the assembly when the fastener is secured to bone. Specifically, the engagement of the threads prevents the coupling element from moving relative to the fastener when driving the fastener into bone, thereby simplifying installation of the fasteners.

These and other objects, features and advantages of the present invention will be more readily apparent from the detailed description of preferred embodiments set forth below, taken in conjunction with the accompanying drawings.

In other preferred embodiments, a coupling element for a stabilizing assembly desirably includes an upper end and a lower end, a rod receiving opening adapted to receive a stabilizing rod, a bore extending through the lower end of the coupling element for receiving a fastener having a head with a first radial surface of a first diameter, and a seat adjacent the lower end of the coupling element adapted to engage an underside of the head of the fastener. The coupling element preferably includes threads extending from the upper end toward the lower end of the coupling element, and an annular lip between the threads and the seat of the coupling element, whereby the annular lip has a second diameter that is less than the first diameter of the first radial surface of the head.

In still other preferred embodiments, a coupling element for a stabilizing assembly includes an upper end and a lower end remote therefrom, and a rod receiving opening adapted to receive a stabilizing rod. The coupling element preferably has an exterior surface and an interior surface defining a central bore extending through the lower end of the coupling element. A seat adjacent the lower end of the coupling element is desirably adapted to engage an underside of a head of the fastener, whereby the coupling element includes one or more cuts between the rod-receiving opening and the exterior surface thereof for minimizing the width of the coupling element. Although the present invention is not limited by any particular theory of operation, it is believed that providing cuts at the edge of the rod receiving opening reduces the width of the coupling element so that more coupling elements may be fit onto a given length of a stabilizing rod. The cuts also minimize the sharp edges on the coupling element, thereby reducing the chance that the coupling element will irritate a patient's tissue and/or cutting a surgeon's glove.

These and other objects, features and advantages of the present invention will be more readily apparent from the detailed description of preferred embodiments set forth below, taken in conjunction with the accompanying drawings.

BRIEF DESCRIPTION OF THE DRAWINGS

FIG. 3B shows an expanded view of a portion of the fastener shown in FIG. 3A.

FIG. 9A shows the assembly of FIG. 7 after the fastener has been anchored in bone.

FIG. 9B shows an expanded view of a portion of FIG. 9A with the coupling element being pivoted to receive a stabilizing rod.

FIG. 19 shows a coupling element having external screw threads in accordance with another preferred embodiment of the present invention.

DETAILED DESCRIPTION

Figure 1:
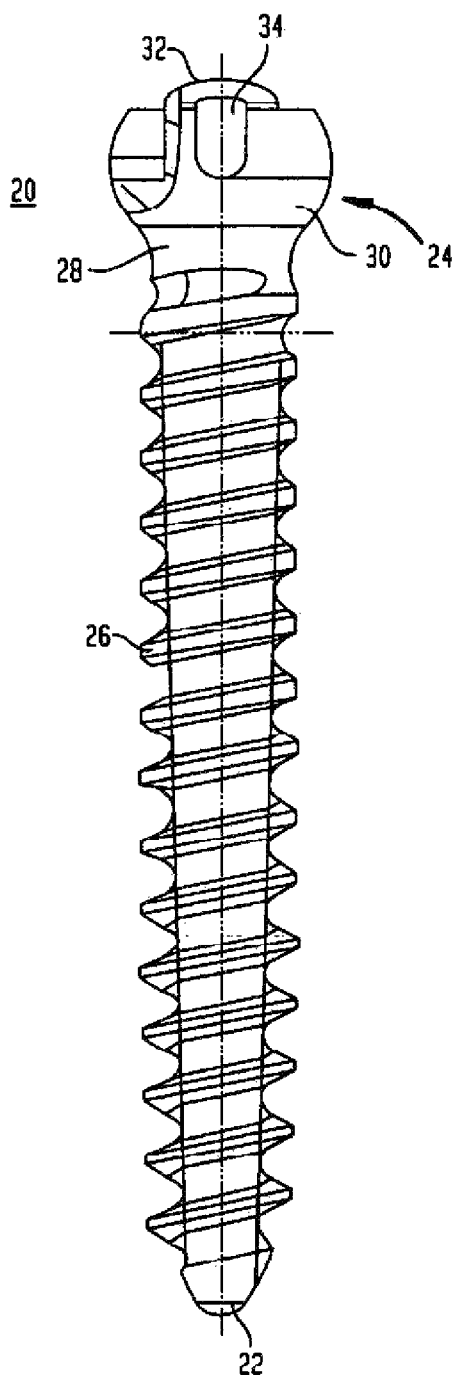
FIG. 1 shows a front elevation view of a fastener for a stabilizing assembly, in accordance with certain preferred embodiments of the present invention.

Referring to FIG. 1, in accordance with certain preferred embodiments of the present invention, a pedicle screw assembly includes a fastener 20, such as a screw fastener having a tip end 22 for insertion into bone and a head 24 at an upper end thereof. The screw fastener 20 preferably has external screw threads 26 that extend between the tip end 22 and screwhead 24. The screw threads terminate at a neck 28 preferably located between screwhead 24 and an upper end of the screw threads 26. The neck 28 desirably has a concave surface having a diameter that is less than the diameter of the screw threads. The reduced diameter neck 28 allows the screw fastener 20 to pivot and rotate through a broader range of motion, as will be described in more detail below. The screw fastener, including the external threads 26, neck 28 and screwhead 24, are preferably made of a non-organic material that is durable and that can be implanted in a human body, such as titanium or stainless steel.

Figure 2:
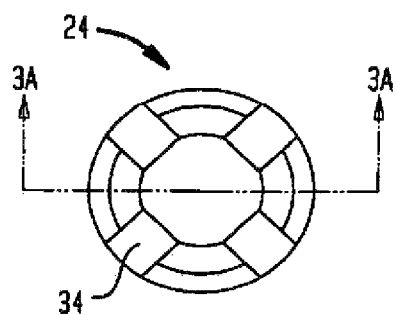
FIG. 2 shows a plan view of the fastener shown in FIG. 1.

Referring to FIGS. 1 and 2, screwhead 24 preferably has an underside 30 defining a first radial surface and a top side 32 defining a second radial surface. Screwhead 24 also desirably includes one or more grooves 34 that extend in a direction substantially parallel to the longitudinal axis of screw fastener 24. Referring to FIG. 2, in one preferred embodiment, screwhead 24 includes a plurality of grooves 34 evenly spaced from one another and extending around the outer perimeter of screwhead 24. The top surface 32 of screwhead 24 is preferably centered on the plurality of grooves 34.

Figure 3A:
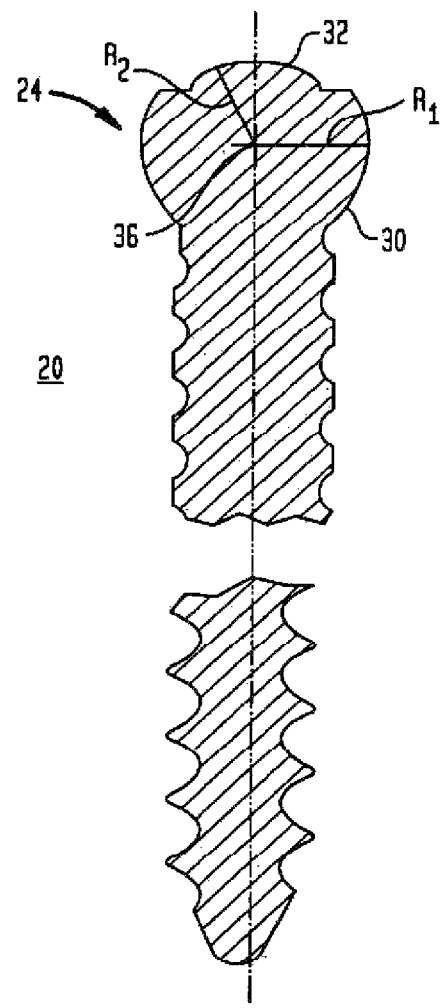
FIG. 3A shows a fragmentary, cross-sectional view of the fastener shown in FIG. 2 taken along line IIIA-IIIA of FIG. 2.

Referring to FIGS. 3A and 3B, screwhead 24 includes a center 36, whereby the underside 30 of screwhead 24 defines the first radial surface having a radius $R_1$ from center 36. Screwhead 24 includes top surface 32 having second radial surface at a second radius $R_2$ from center 36. The plurality of grooves 34 are preferably adapted to receive prongs of a driver used to screw the screw fastener into bone, as will be described in more detail below.

Figure 4:
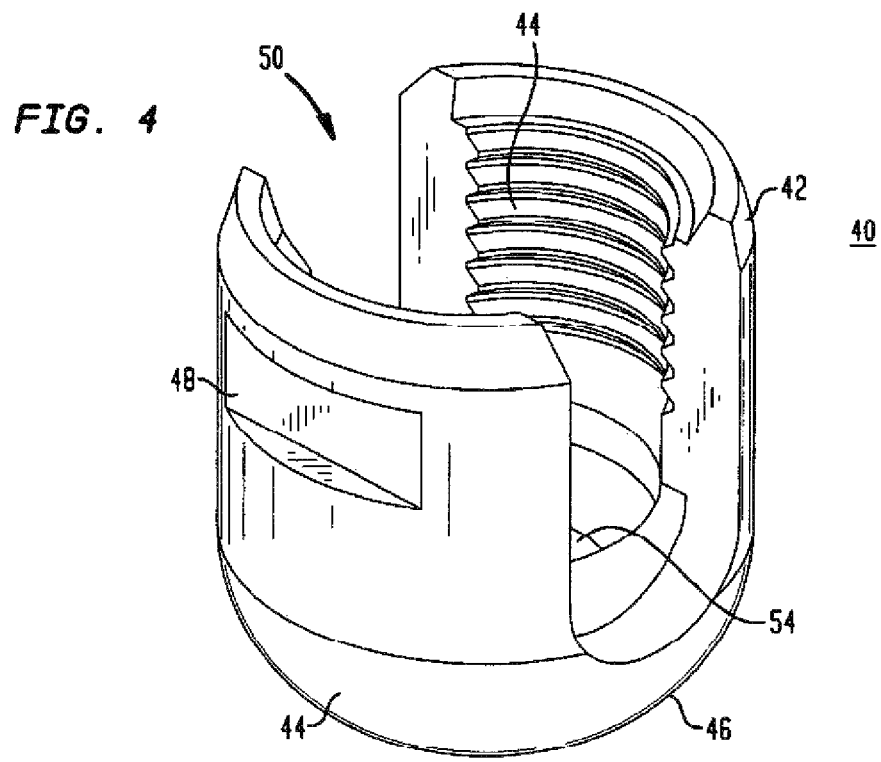
FIG. 4 shows a perspective view of a coupling element for a stabilizing assembly, in accordance with certain preferred embodiments of the present invention.
Figure 5:
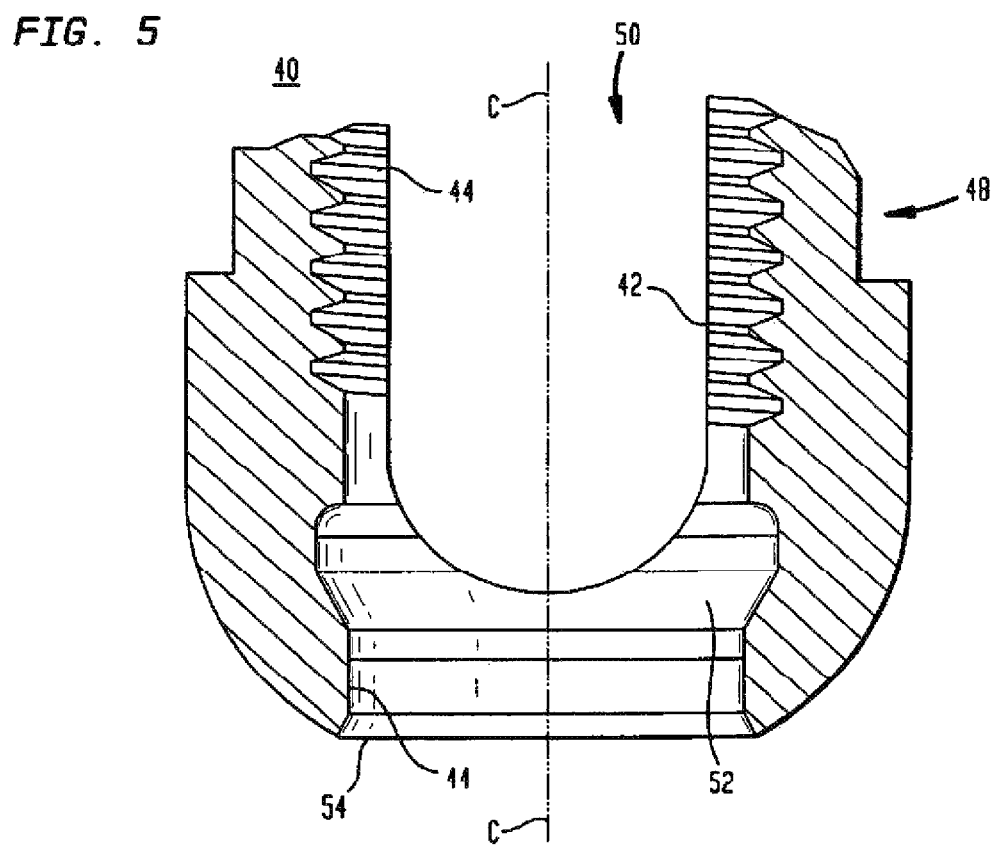
FIG. 5 shows a fragmentary, cross-sectional view of the coupling element shown in FIG. 4.

Referring to FIGS. 4 and 5, pedicle screw assembly also includes a coupling element 40 for coupling an orthopedic stabilizing rod with the screw fastener shown in FIGS. 1-3B. Coupling element 40 is preferably made of an inert material such as titanium or stainless steel. Coupling element 40 has an upper end 42, a lower end 44, and a longitudinal axis C-C extending between the upper and lower ends. Coupling element 40 also preferably has an outer surface 46 including a convex surface at the lower end 44 thereof and a cylindrical surface at the upper end thereof. Outer surface 46 also preferably includes one or more grooves 48 formed therein so that coupling element 40 may be grasped and/or maneuvered using a securing element or tool, such as a persuader instrument used to seat the orthopedic rod in the pedicle screw assembly. The grooves preferably extend in directions substantially perpendicular to the longitudinal axis C-C of coupling element 40.

The coupling element 40 has a bore 50 for receiving the screw fastener, the bore extending along the longitudinal axis C-C of coupling element 40. The bore 50 defines an inner surface of coupling element 40 and has internal threads 44 extending from the upper end 42 of the coupling element toward a cavity 52 adjacent lower end 44. The lower end of cavity 52 preferably has a conical-shaped seat 54 including sidewalls tapering inwardly toward the lower end 44. In other embodiments, the threads on the coupling element may be external threads.

Figure 6B:
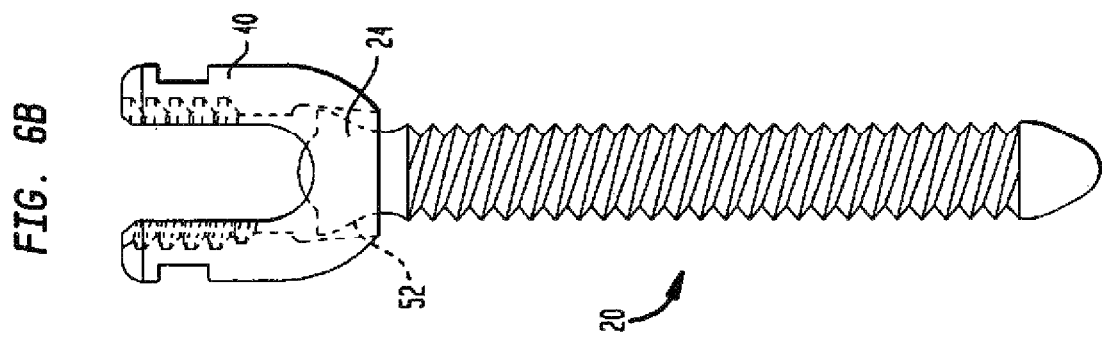
FIGS. 6A and 6B show a method of assembling the fastener of FIGS. 1-3B with the coupling element of FIGS. 4-5, in accordance with certain preferred embodiments of the present invention.
Figure 6A:
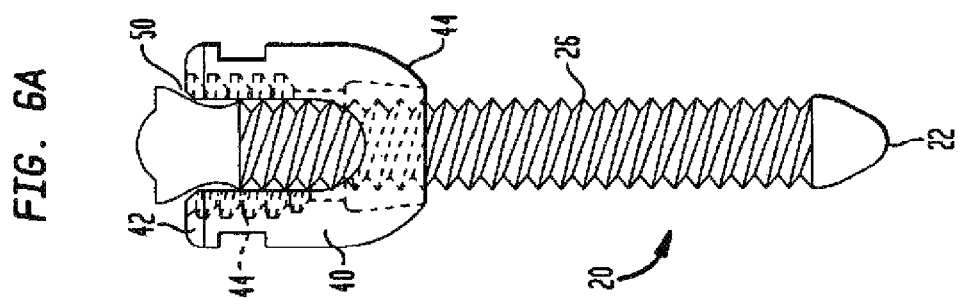
Figure 8:
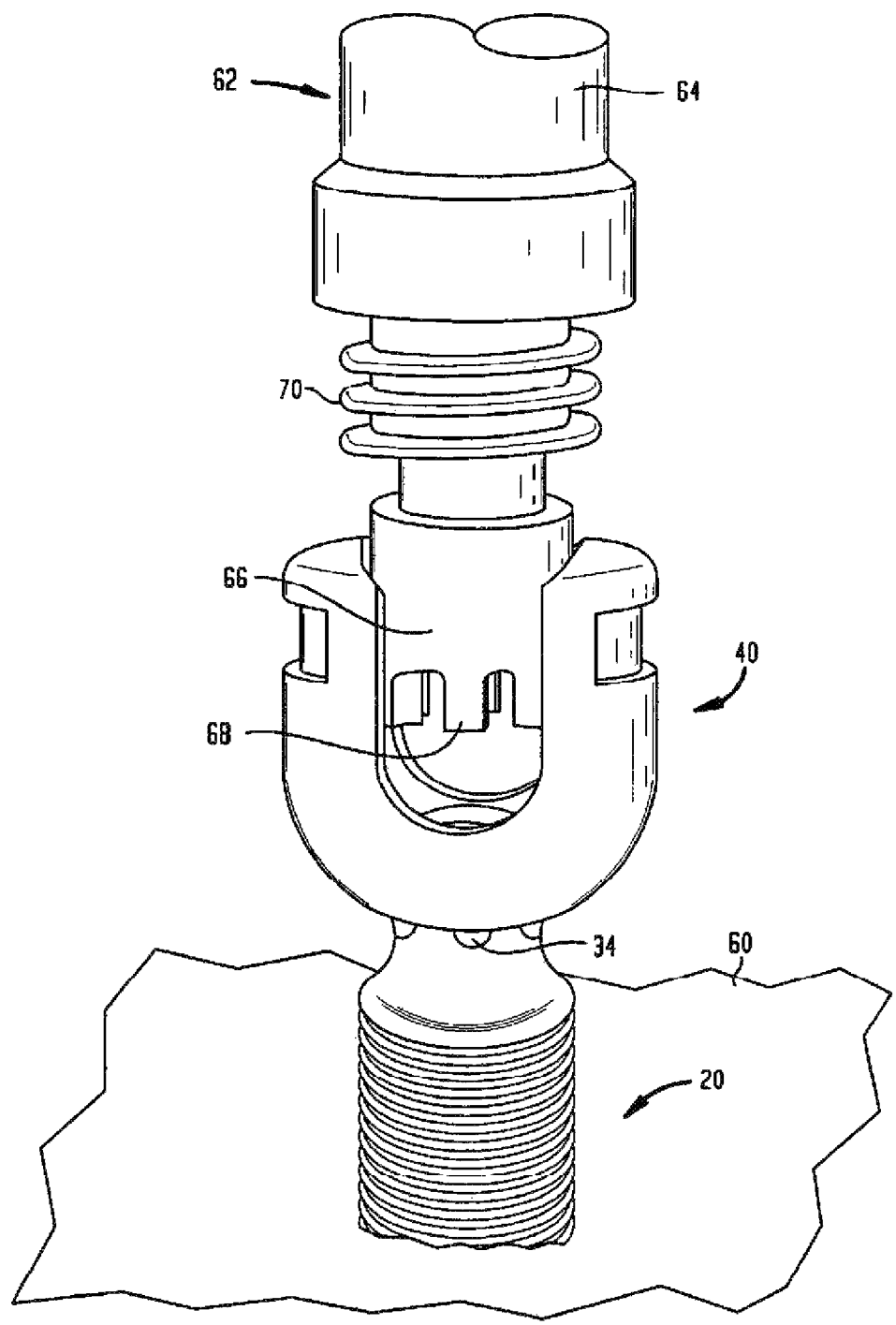
FIG. 8 shows a perspective view of a driver for engaging the assembly of FIG. 7 for driving the fastener into bone, in accordance with certain preferred embodiments of the present invention.

FIGS. 6A and 6B show one preferred method for assembling screw fastener 20 with coupling element 40. Referring to FIG. 6A, tip end 22 of screw fastener 20 is passed through bore 50 of coupling element 40 from the upper end 42 toward the lower end 44 of the coupling element so that the threaded portion of screw fastener passes through bore 50. The threaded portion 26 of screw fastener 20 is able to pass freely through bore 50 because the threaded portion 26 has an outer diameter that is less than the internal diameter of the internal threads 44 of coupling element 40. Referring to FIG. 6B, screw fastener 20 continues to be inserted toward the lower end of coupling element 40 until screwhead 24 is disposed within cavity 52 of coupling element 40 and the underside of screwhead engages the seat of coupling element.

Figure 7:
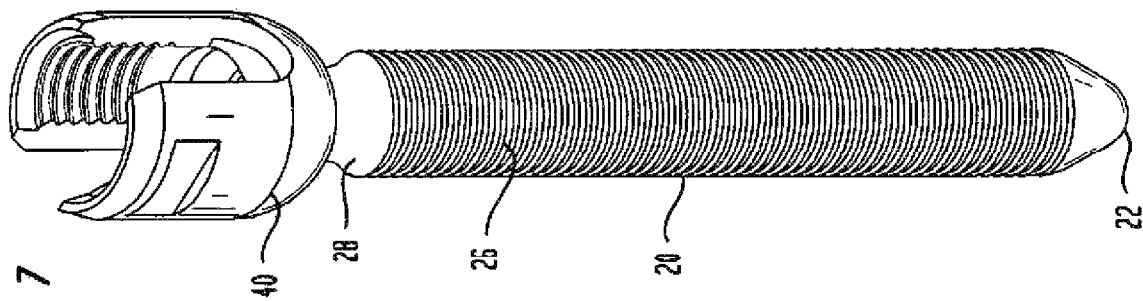
FIG. 7 shows a perspective view of the assembly shown in FIG. 6B.

Referring to FIG. 7, after the screw fastener 20 has been assembled with coupling element 40, the neck 28 of screw fastener 20 is free to pivot and rotate relative to coupling element. As mentioned above, neck 28 preferably has a reduced diameter and may also have a concave outer surface so that the screw fastener 20 and coupling element, may pivot relative to one another over a broader range of angles.

After screw fastener 20 and coupling element, have been assembled together, the subassembly is ready to be inserted into bone 60. In a first step, the screw fastener 20 may be anchored to bone 60 by drilling a pilot hole into the bone. The tip end (not shown) of screw fastener 20 may then be placed in the pilot hole and the screw fastener screwed into bone 60 using a driver or tool. One preferred driver 62 for driving screw fastener 20 into bone 60 includes a rotatable shaft 64 having a lower end 66 with a plurality of downwardly extending prongs 68. The prongs 68 are sized for fitting into the grooves 34 of the screwhead (not shown) of screw fastener 20. Upon rotation of shaft 64, prongs 68 engage grooves 34 of screw fastener 20 for rotating screw fastener 20 and screwing the fastener into bone 60. Driver 62 may also include external threads 70, preferably between shaft 64 and prongs 68. External threads 70 are designed for threadably mating with the internal threads 44 of coupling element 40 (FIGS. 4-5). The mating engagement of the external threads 70 of driver and the internal threads 44 of coupling element 40 generally stabilizes the pedicle screw assembly when driving the screw fastener 20 into bone 60.

Referring to FIGS. 9A and 9B, after screw fastener 20 is anchored in bone 60, coupling element 40 remains free to pivot and rotate relative to the screw fastener so that an orthopedic stabilizing rod 72 may be positioned within the rod receiving opening 74 of coupling element 40. Rod receiving opening 74 preferably includes a U-shaped opening extending from the top 42 of coupling element 40. Moreover, after screw fastener 20 has been fully inserted into bone, a gap exists between the lower end 44 of coupling element 40 and bone 60. The gap facilitates pivotal and rotational movement of coupling element 40 relative to screw fastener 20. The coupling element 40 may then be moved (e.g. pivoted) by engaging grooves 48 with a tool or by grasping the outer body portion of the coupling element. Coupling element 40 would then be pivoted and/or rotated so that an orthopedic rod 72 can be positioned in the rod receiving opening 74, as shown in FIG. 9B.

Figure 9C:
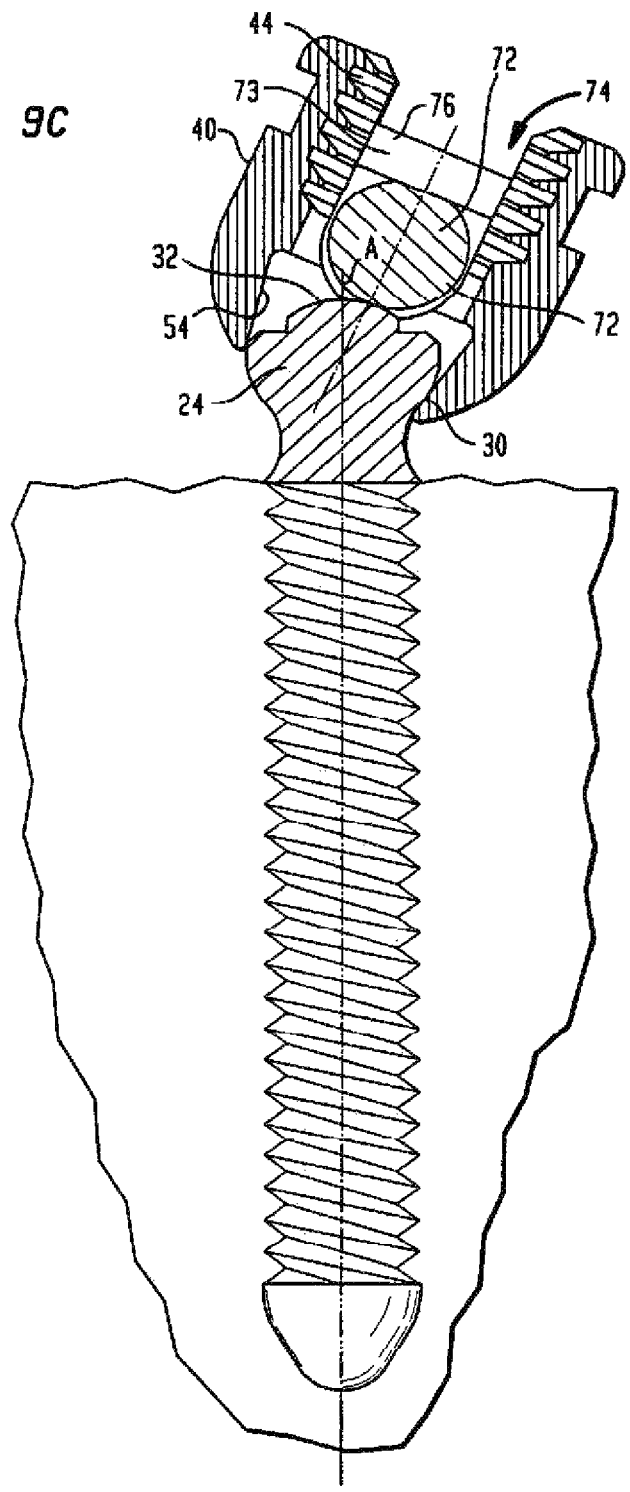
FIG. 9C shows a stabilizing rod secured to the coupling element by a set screw, in accordance with certain preferred embodiments of the present invention.

Referring to FIG. 9C, after stabilizing rod 72 has been positioned within coupling element 40, a set screw 76 having external threads (not shown) is screwed into the internal threads 44 of coupling element 40. Set screw 76 continues to be threaded into the internal threads 44 until an underside 78 of set screw 76 abuts against stabilizing rod 72. Set screw 76 is then further rotated into internal threads 44 for locking stabilizing rod 72 in rod receiving channel 74. The tightened set screw 76 applies a downward force through rod 72 onto the second radial surface at the top side 32 of screwhead 24. The downward force applied to the second radial surface of screwhead 24 forces the first radial surface at the underside 30 of screwhead 24 into the conical-shaped seat 54 of coupling element 40. Engagement of the first radial surface at the underside 30 of screwhead 24 with the conical-shaped seat 54 creates a spherical surface/conical surface friction lock that locks the coupling element 40 relative to the screwhead 24, thereby preventing further pivotal and rotary movement of coupling element 40 and screw fastener 20 relative to one another. Although the present invention is not limited by any particular theory of operation, it is believed that the engagement of the spherical surface of the screwhead with the conical seat of the coupling element dramatically improves the locking force exerted at the interface of the screwhead and the coupling element.

Figure 10:
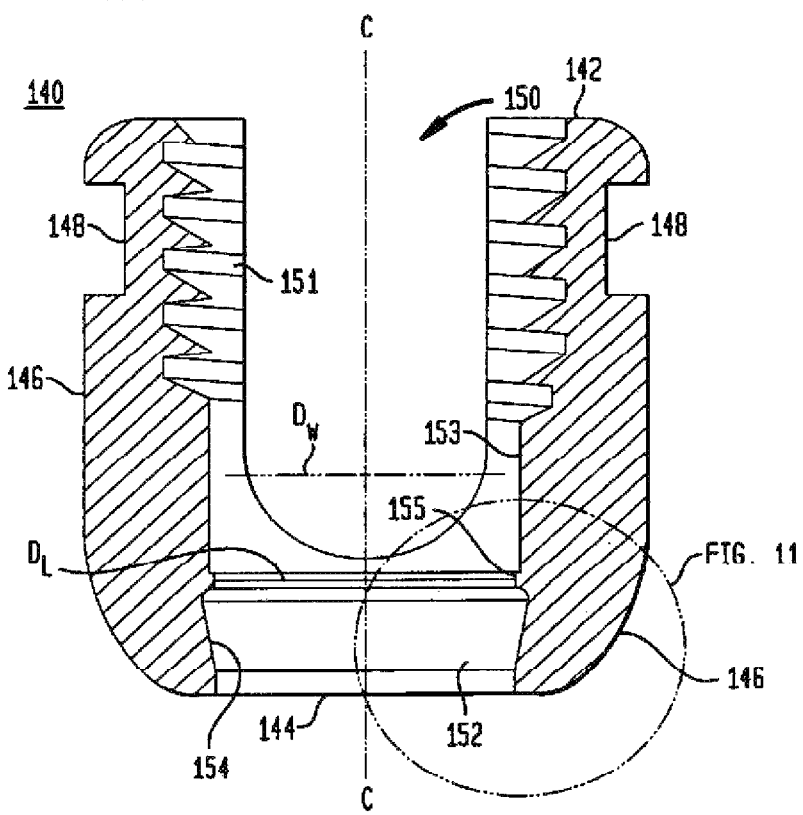
FIG. 10 shows a cross-sectional view of a coupling element, in accordance with further preferred embodiments of the present invention.
Figure 12:
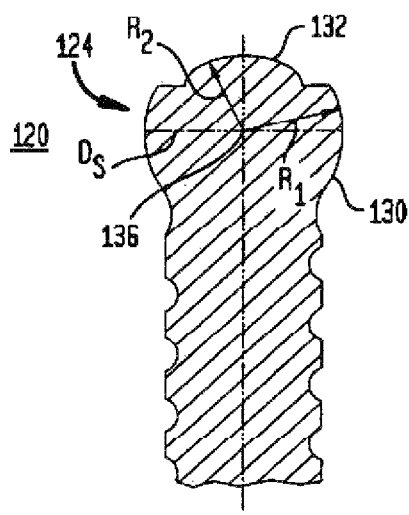
FIG. 12 shows a fragmentary view of a fastener, in accordance with certain preferred embodiments of the present invention.

Referring to FIG. 10, in accordance with other preferred embodiments of the present invention, a coupling element 140 for a stabilizing assembly includes an upper end 142 and a lower end 144. Coupling element 140 also includes an outer surface 146 extending between upper and lower ends 142, 144, the outer surface 146 including one or more grooves 148. Coupling element also includes a centrally located bore 150 extending between the upper end 142 and lower end 144 along longitudinal axis C-C. Bore 150 is surrounded by interior threads 151 extending from the upper end 142 toward the lower end 144. Coupling element 140 also includes a cavity 152 adjacent lower end 144, the cavity including a conical-shaped seat 154 having sidewalls that taper inwardly toward the lower end 144 of coupling element 140. Coupling element 140 also preferably includes an interior wall 153 having diameter $D_W$ between interior threads 151 and cavity 152, and a lip 155 between interior wall 153 and cavity 152. The lip 155 has a diameter $D_L$ that is less than the diameter $D_W$ of interior wall 153. As shown in FIG. 12, the outer diameter $D_S$ of the first radial surface 130 of screwhead 124 is greater than the diameter $D_L$ of the lip 155 of coupling element. As a result, lip 155 serves as a detent that holds fastener 120 in the cavity 152 of coupling element 140 after the screwhead of fastener 120 has been assembled with the coupling element 140.

Figure 11:
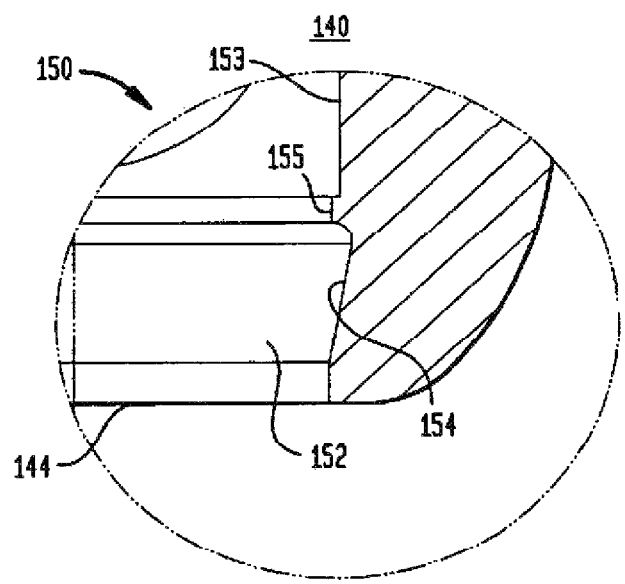
FIG. 11 shows a fragmentary view of the coupling element shown in FIG. 10.

FIG. 11 shows a magnified view of a portion of the coupling element 140 shown in FIG. 10. As described above, coupling element 140 includes bore 150 extending from an upper end (not shown) toward lower end 144 thereof, and an interior wall 153 extending between internal threads 151 and cavity 152. Cavity 152 includes conical-shaped seat 154 having inwardly tapering sidewalls 154. Coupling element 140 includes lip 155 positioned between interior wall 153 and cavity 152. Lip 155 has a diameter $D_L$ that is less than the diameter $D_W$ of the interior wall 153 of coupling element 140.

FIG. 12 shows screw fastener 120 having screwhead 124 at an upper end thereof, the screwhead including a first radial surface 130 at an underside thereof and a second radial surface 132 at a top side of screwhead 124. Screwhead 124 includes a center 136, a first radial surface 130 from center 136 having a radius $R_1$ and a second radial surface 132 from center 136 having a second radius $R_2$, whereby $R_1$ is greater than $R_2$. The first radial surface of screwhead 124 defines an outer diameter $D_S$ that is two times the length of $R_1$.

Figure 13A:
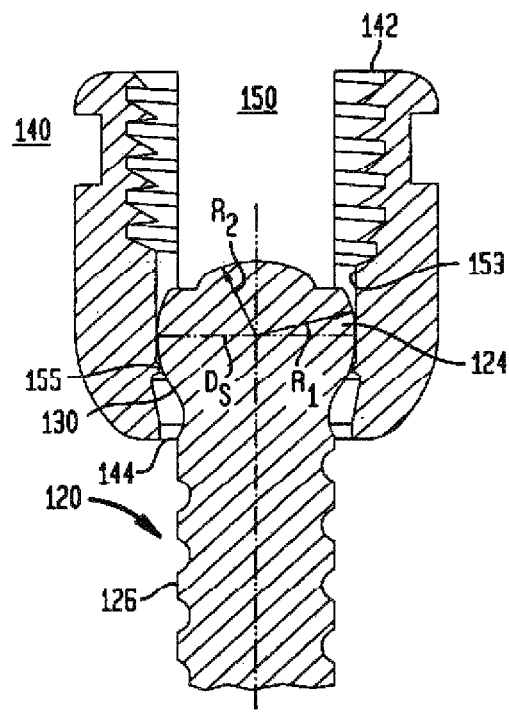
FIGS. 13A and 13B show a method of assembling the fastener to a coupling element, in accordance with certain preferred embodiments of the present.
Figure 13B:
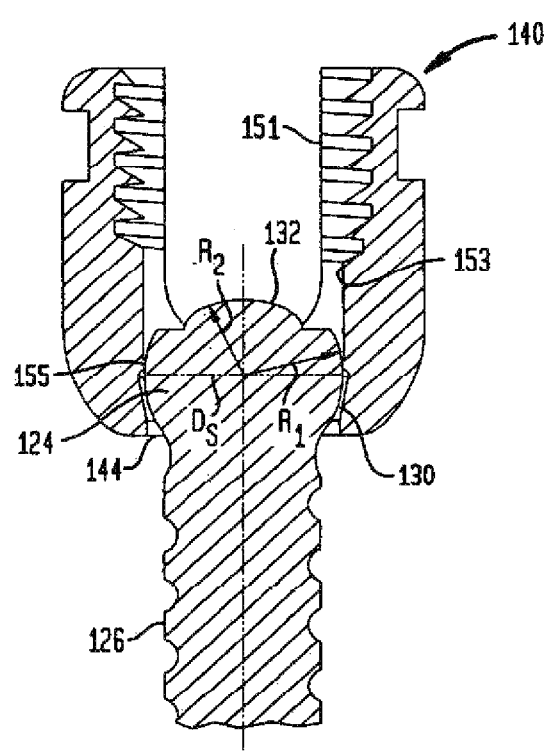

FIGS. 13A and 13B show screw fastener 120 being assembled with the coupling element 140 shown in FIGS. 10 and 11. As mentioned above, coupling element 140 includes lip 155 having a diameter $D_L$ that is less than the diameter $D_S$ of the first radial surface 130 of screwhead 124, however, the outer diameter $D_S$ of the first radial surface 130 of screwhead 124 is less than the inner diameter of inner wall 153.

Referring to FIGS. 13A and 13B, during assembly of screw fastener 120 to coupling element 140, the screw fastener 120 is passed through bore 150 so that screw threads 126 pass through the opening at lower end 144 of coupling element 140. Because the outer diameter $D_S$ of screwhead 124 is less than the inner diameter of inner wall 153, screwhead 124 passes easily through bore 150 until first radial surface 130 engages lip 155. Because the inner diameter $D_L$ of lip 155 is less than the outer diameter $D_S$ of the first radial surface 130 of screwhead 124, the lip 155 acts as a detent and the screwhead must be forced through the reduced diameter of lip 155. Referring to FIG. 13B, after the outer diameter $D_S$ of screwhead 124 has passed by lip 155, the screwhead is retained within cavity 152 by lip 155, with coupling element 140 pivotable relative to screwhead 124 for capturing a stabilizing rod. After stabilizing rod is captured within the U-shaped opening of coupling element 140, a set screw (not shown) may be threaded into internal threads 151 of coupling element 140 for capturing the stabilizing rod within the U-shaped opening. The set screw is then preferably tightened for exerting a downward force upon the stabilizing rod which, in turn, applies a force to the second radial surface 132 of screwhead 124. The downward force on the second radial surface 132 forces the first radial surface 130 into the conical-shaped seat of coupling element for locking the screwhead and coupling element relative to one another.

Figure 14:
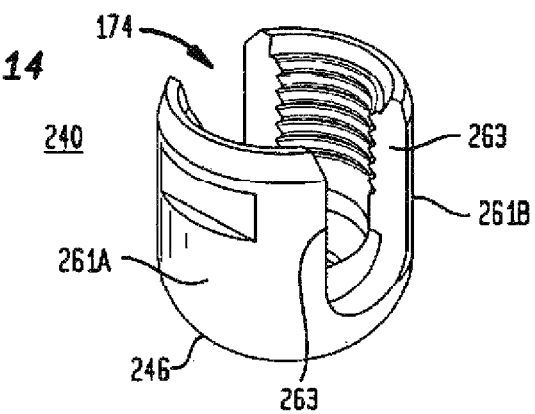
FIG. 14 shows a perspective view of a coupling element, in accordance with further preferred embodiments of the present invention.
Figure 15:
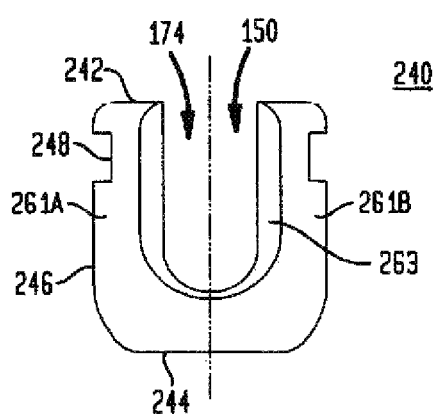
FIG. 15 shows a front elevation view of the coupling element of FIG. 14.
Figure 16:
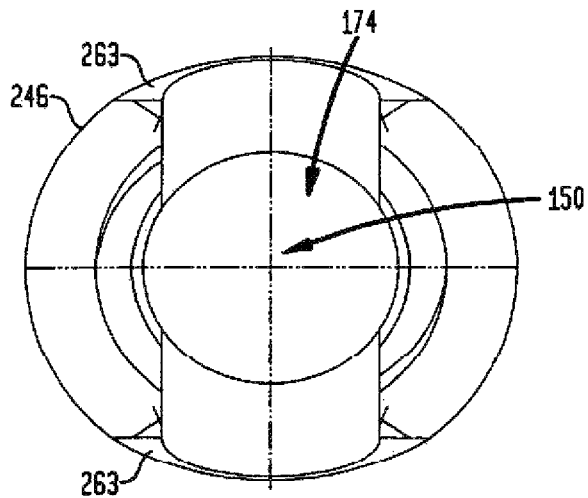
FIG. 16 shows a plan view of the coupling element shown in FIGS. 14 and 15.

FIGS. 14-16 show a coupling element 240 in accordance with further preferred embodiments of the present invention. Coupling element 240 includes upper end 242, lower end 244 and outer wall 246 extending between upper and lower ends 242, 244. The outer surface 246 of coupling element 240 includes grooves 248 on opposing arms thereof. Coupling element 240 has central bore 150 extending between upper and lower ends thereof. Coupling element 240 has a first arm 261A and a second arm 261B on either side of U-shaped rod-receiving opening 174, the U-shaped rod-receiving opening being adapted to receive a stabilizing rod (not shown). The edges of the U-shaped opening include cuts 263 formed therein. The cuts 263 reduce the profile or width of the coupling element, thereby minimizing interference with other coupling elements when a series of coupling elements are connected with a stabilizing rod. The cuts 263 allow the coupling elements 240 to be packed more tightly together and to be secured over each vertebrae, thereby improving fusion of a spinal segment. Although the present invention is not limited by any particular theory of operation, it has been observed that some patients have relatively small vertebrae, making it difficult to secure a coupling element over each vertebrae. As a result, some of the vertebrae may not have a section of the stabilizing assembly attached thereto, a situation that may adversely affect stabilization and fusion of a spine segment because the entire portion of the spine segment is not being stabilized. In addition, the cuts 263 minimize the occurrence of sharp edges on the coupling element that may irritate a patient's tissue or cut through a surgeon's surgical glove.

Figure 17:
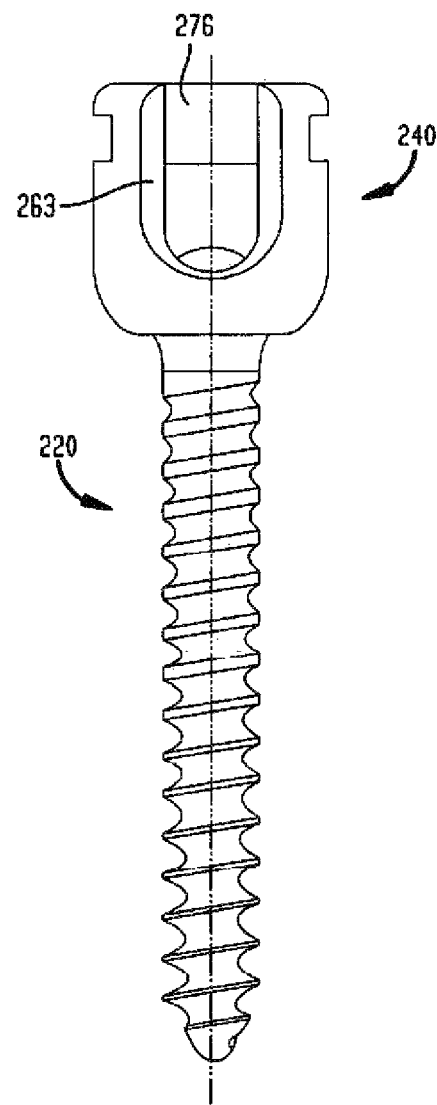
FIG. 17 shows a front elevation view of a screw fastener coupled with a coupling element, in accordance with further preferred embodiments of the present invention.

FIG. 17 shows a front elevation view of the coupling element 240 of FIGS. 14-16 assembled with screw fastener 220. Coupling element 240 includes internal threads (not shown) for receiving set screw 276. Coupling element 240 includes cuts 263 for minimizing the profile of the coupling element and reducing the occurrence of sharp edges.

Figure 18:
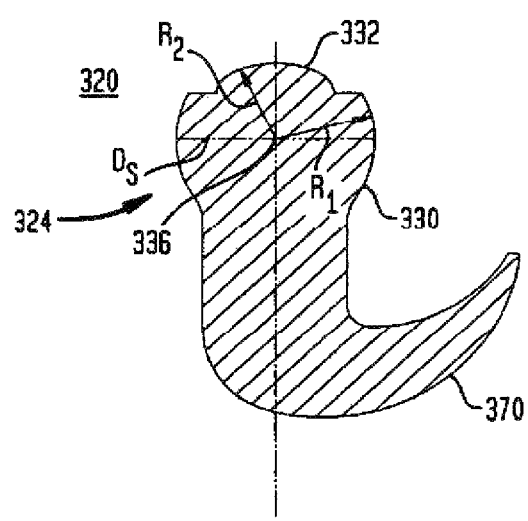
FIG. 18 shows a fastener for a stabilizing assembly in accordance with further preferred embodiments of the present invention.

FIG. 18 shows a fastener 320 in accordance with another embodiment of the present invention. Fastener 320 includes head 324 having a first radial surface 330 having radius $R_1$ from center 336 and second radial surface 332 having radius $R_2$ from center 336. The first radius, $R_1$, is greater than the second radius $R_2$. Fastener 320 includes hook 370 for securing the fastener to bond (not shown).

FIG. 19 shows an assembly in accordance with another embodiment of the present invention including a coupling element 440 having external threads 444 extending from an upper end thereof. The assembly also includes a locking element 476 having internal threads 477 adapted to thread onto the external threads 444 of coupling element 440.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stabilizing assembly comprising:
a fastener having
an upper end and a lower end,
a head at the upper end, said head including a center and at least a portion of said head having a radius of curvature from the center of the head, and
at least one anchoring element between the upper and lower ends thereof; and
a coupling element having
an outer surface, an interior wall having a diameter, an upper end and a lower end,
a rod receiving opening adapted to receive a stabilizing rod,
a bore extending through the lower end for receiving said fastener,
a cavity adjacent to said lower end,
a seat, and
an annular lip located between the upper end of said coupling element and the seat of said coupling element wherein said annular lip has a diameter less than the diameter of said interior wall and a diameter of an adjacent portion of said cavity,
wherein the portion of said head having the radius of curvature is engagable with the seat when said fastener is positioned in the bore, and wherein the stabilizing rod contacts said head so that the stabilizing rod forces the portion of said head against the seat of said coupling element.

2. The stabilizing assembly of claim 1, wherein the portion of said head of the fastener having the radius of curvature includes an underside of said head, the radius of curvature defining a first radius.

3. The stabilizing assembly of claim 2, wherein said head further comprises a top side, the top side having a second radius of curvature from the center defining a second radius.

4. The stabilizing rod of claim 3, wherein the first radius is larger than the second radius.

5. The stabilizing assembly of claim 1, wherein the seat of said coupling element includes inwardly tapering conical-shaped sidewalls.

6. The stabilizing assembly of claim 1, wherein said coupling element includes an outer surface and one or more cuts between the rod-receiving opening and the outer surface.

7. The stabilizing assembly of claim 1, wherein said annular lip has a radius less than the radius of curvature of said portion of said head, wherein the annular lip prevents the fastener from passing into the upper end.

8. The stabilizing assembly of claim 1, wherein said fastener is a screw fastener having screw threads and a neck having a reduced diameter between the head of said fastener and the screw threads.

9. The stabilizing assembly of claim 1, further comprising a locking element associated with said coupling element to apply a force upon a stabilizing rod positioned in said rod receiving opening, wherein said stabilizing rod is in direct contact with and applies a force upon the head for forcing the head against the seat for preventing further pivotal and rotational movement of said fastener and said coupling element relative to one another.

10. The stabilizing assembly of claim 1, further comprising at least two parallel grooves formed on the outer surface of the coupling element.

11. A stabilizing assembly comprising:
a fastener having
an upper end and a lower end,
a head at the upper end, said head including a center and at least a portion of said head having a radius of curvature from the center of the head and
at least one anchoring element between the upper and lower ends thereof; and
a coupling element having
an outer surface, an interior wall having a diameter, an upper end and a lower end,
a rod receiving opening adapted to receive a stabilizing rod, a bore extending through the lower end for receiving said fastener, a cavity adjacent to said lower end, a seat, and an annular lip located between the upper end of said coupling element and the seat of said coupling element wherein said annular lip has a diameter less than the diameter of said interior wall and a diameter of an adjacent portion of said cavity, wherein the portion of said head having the radius of curvature is engagable with the seat when said fastener is positioned in the bore, and wherein said coupling element includes one or more cuts between the rod-receiving opening and an outer surface thereof for minimizing the width of said coupling element.

12. The stabilizing assembly of claim 11, wherein the stabilizing rod contacts said head so that the stabilizing rod forces the portion of said head against the seat of said coupling element.

13. The stabilizing assembly of claim 11, wherein the portion of said head of the fastener having the radius of curvature includes an underside of said head, the radius of curvature defining a first radius.

14. The stabilizing assembly of claim 13, wherein said head further comprises a top side, the top side having a second radius of curvature from the center defining a second radius.

15. The stabilizing assembly of claim 14, wherein the first radius is larger than the second radius.

16. The stabilizing assembly of claim 11, wherein the seat of said coupling element includes inwardly tapering conical-shaped sidewalls.

17. The stabilizing assembly of claim 11, wherein said annular lip has a radius less than the radius of curvature of said portion of said head, wherein the annular lip prevents the fastener from passing into the upper end.

18. The stabilizing assembly of claim 11, further comprising a locking element associated with said coupling element to apply a force upon a stabilizing rod positioned in said rod receiving opening, wherein said stabilizing rod is in direct contact with and applies a force upon the head for forcing the head against the seat for preventing further pivotal and rotational movement of said fastener and said coupling element relative to one another.

19. The stabilizing assembly of claim 11, wherein said fastener is a screw fastener having screw threads and a neck having a reduced diameter between the head of said fastener and the screw threads.

20. The stabilizing assembly of claim 11, further comprising at least two parallel grooves formed on the outer surface of the coupling element.

\* \* \* \* \*